United States Patent

Hoede et al.

[11] Patent Number: 6,138,499
[45] Date of Patent: Oct. 31, 2000

[54] EXHAUST EMISSION ANALYSIS SYSTEM INCORPORATING PULSE DAMPENING

[75] Inventors: Christiaan Hoede, Diemen; Raymond M.P.M. Mulder, Amstelveen, both of Netherlands

[73] Assignee: Sun Electric Europe B.V., Amsterdam, Netherlands

[21] Appl. No.: 09/141,741

[22] Filed: Aug. 27, 1998

[51] Int. Cl.[7] .................................................. G01N 1/10
[52] U.S. Cl. ...................... 73/23.31; 73/23.2; 73/31.05; 138/30
[58] Field of Search ............................. 73/23.31, 31.05, 73/23.2; 138/30; 137/863; 123/41.5, 41.58

[56] References Cited

U.S. PATENT DOCUMENTS

| | | |
|---|---|---|
| 2,185,023 | 12/1939 | Crane . |
| 2,216,374 | 10/1940 | Martin . |
| 2,233,804 | 3/1941 | Bourne . |
| 2,867,240 | 1/1959 | Bent . |
| 2,883,180 | 4/1959 | Moulton ..................................... 138/30 |
| 3,159,182 | 12/1964 | Peters . |
| 3,895,915 | 7/1975 | Haldeman ................................. 23/234 |
| 4,177,023 | 12/1979 | Kamiya et al. . |
| 4,452,276 | 6/1984 | Hozumi et al. . |
| 4,508,598 | 4/1985 | Giner ........................................ 204/1 |
| 4,543,997 | 10/1985 | Kishimoto . |
| 4,548,240 | 10/1985 | Graham . |
| 4,615,320 | 10/1986 | Fehrenbach et al. . |
| 4,660,524 | 4/1987 | Bertsch et al. ............................ 138/30 |
| 4,911,204 | 3/1990 | Martin . |
| 5,036,879 | 8/1991 | Ponci . |
| 5,110,747 | 5/1992 | Pataschnick et al. .................... 436/133 |
| 5,176,178 | 1/1993 | Schurter et al. . |
| 5,419,178 | 5/1995 | Decker et al. .......................... 73/23.31 |
| 5,476,448 | 12/1995 | Urich . |
| 5,562,002 | 10/1996 | Lalin ........................................ 73/241 |

*Primary Examiner*—Hezron Williams
*Assistant Examiner*—Michael Cygan
*Attorney, Agent, or Firm*—Seyfarth Shaw

[57] ABSTRACT

An automotive engine exhaust emissions analysis system includes a pump for moving emissions through a conduit to a nitric oxide sensor through a relatively low-volume expansion chamber which is bounded in part by an unconstrained elastic membrane exposed to ambient air.

10 Claims, 2 Drawing Sheets

EXHAUST EMISSION ANALYSIS SYSTEM INCORPORATING PULSE DAMPENING

BACKGROUND OF THE INVENTION

The present invention relates to surge or pulse suppression in fluid flow systems and, in particular, to gas analyzer systems, such as analyzers for automotive exhaust emissions.

In recent years government-mandated exhaust emissions standards for automotive internal combustion engines have resulted in various programs for testing or analyzing automotive exhaust emissions for compliance with the standards. These programs commonly involve the use of gas analyzer systems for analyzing the contents of exhaust emissions. Such gas analyzers commonly employ a pump for moving the stream of emissions through a conduit to an analysis apparatus, which commonly includes one or more sensors for detecting the presence of different constituents of the exhaust emissions. One such sensor is a nitric oxide (NO) sensor, which is in the nature of an electrochemical cell for measuring the quantity of nitric oxide in the exhaust emissions. Certain NO cells are very sensitive to pulsations in the gas stream incident on the sensor, and such pulsations can adversely affect the accuracy of the readings obtained by the sensor. Thus, pulsations, such as those introduced by the pump in the gas analyzer system, can have an adverse affect on the performance of the NO cell.

It is known to damp pulsations in fluid streams by effectively filtering the frequency of the pulsations. In a gas analyzer, the pulsations have a frequency which is related to the RPM of the pump. Such a filter may include a flow restricter, which is the acoustical equivalent of an electrical resistor, and an expansion chamber, which is the acoustic equivalent of an electrical capacitor. It has been found that it is possible to achieve effective damping of the pump pulsations by either (a) increasing the resistance by increasing the flow restriction, or (b) increasing the volume of the expansion chamber. The relatively large expansion chamber needed to effectively damp the pulsations takes a long time to fill, which leads to a substantial increase in the response time of the measuring system. Most regulations governing gas analyzer systems for automotive exhaust emissions specify maximum response times, and these mandated maximum response times may be exceeded with the large expansion chambers required to effectively damp the pulsations in the gas analyzer system.

SUMMARY OF THE INVENTION

It is a general object of the invention to provide an improved pulse dampening device for fluid flow systems, which avoids the disadvantages of prior devices while affording additional structural and operating advantages.

An important feature of the invention is the provision of a pulse-dampening device of the type set forth which is characterized by a relatively fast response time.

In connection with the foregoing feature, a further feature of the invention is the provision of a device of the type set forth, which utilizes a variable-volume expansion chamber which can increase in volume without a substantial increase in pressure.

In connection with the foregoing features, a further feature of the invention is the provision of a device of the type set forth, which includes an expansion chamber bounded by a flexible and resilient membrane exposed to ambient air.

Still another feature of the invention is the provision of a gas analyzing system incorporating a pulse-dampening device of the type set forth.

Certain ones of these and other features of the invention may be attained by providing a device for dampening pressure surges in a fluid conduit comprising: a housing defining a cavity with an open end and discrete inlet and outlet ports for communication with the conduit, and a flexible and resilient membrane cooperating with the housing to close the open end of the cavity and define an expansion chamber, the membrane having a free outer surface exposed to ambient air.

Other features of the invention may be attained by providing a system for analyzing constituents of exhaust emissions from an internal combustion engine comprising: a conduit adapted to be coupled to the engine for receiving exhaust emissions therefrom, a sensor for sensing a constituent of the emissions, a pump coupled to the conduit for moving the emissions through the conduit to the sensor, and a single expansion chamber coupled in the conduit and defined in part by an unconstrained elastic membrane for dampening pump-induced pulsations in the conduit.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DESCRIPTION OF THE PREFERRED EMBODIMENT

Figure 1:
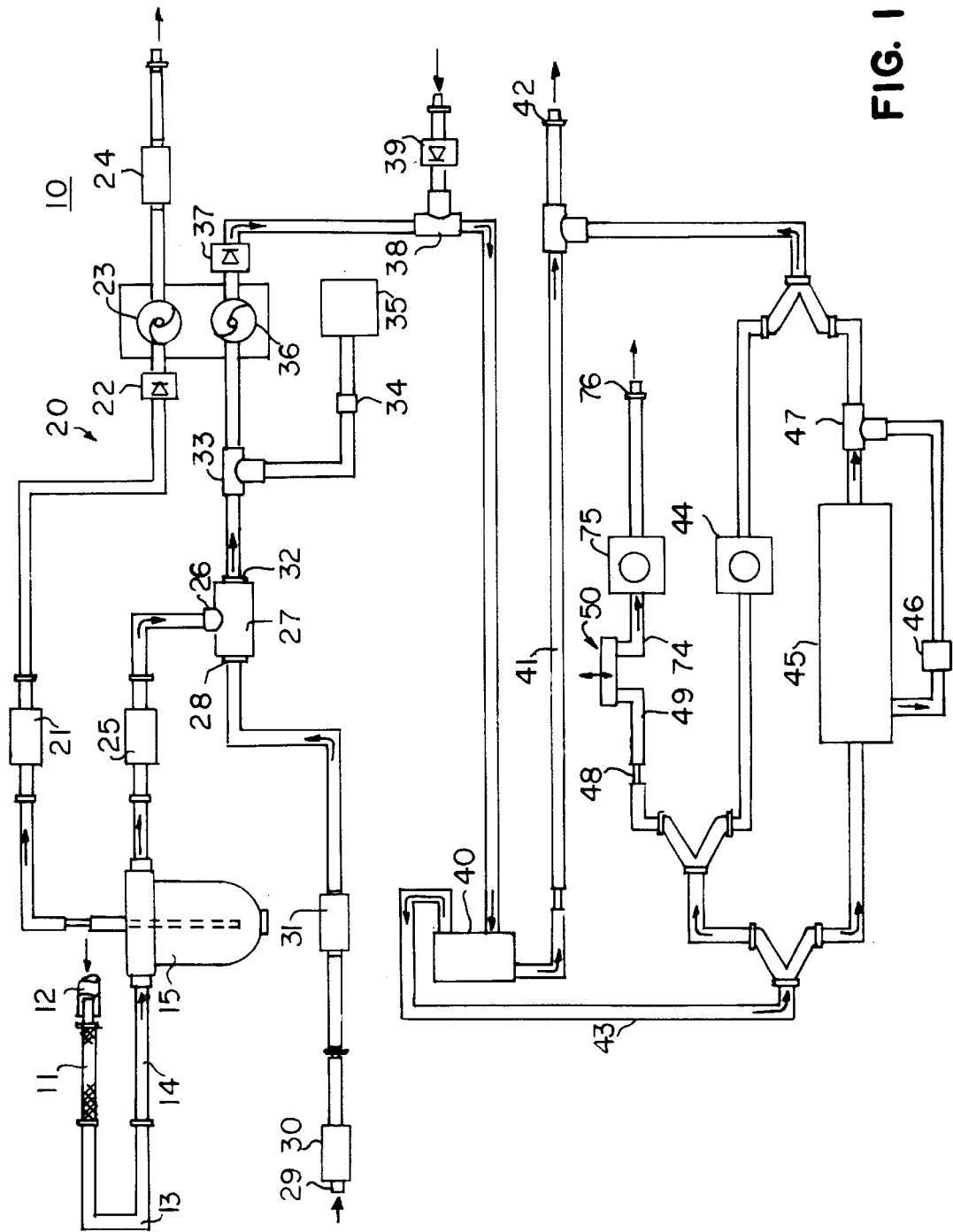
FIG. 1 is a schematic pneumatic diagram of a gas analyzing system for analyzing automotive exhaust emissions, constructed in accordance with and embodying the features of the present invention.

Referring to FIG. 1, there is illustrated a gas analyzer system, generally designated by the numeral 10, incorporating a pulse dampening apparatus in accordance with the present invention. The gas analyzer system 10 is designed for analyzing the exhaust emissions of an automotive internal combustion engine, and includes a probe 11 adapted to fit inside the tail pipe 12 of an associated automotive vehicle (not shown) to collect exhaust emissions therefrom. The collected emissions are fed through a hose 13 and a gas inlet 14 to a filter/separator 15 which separates gaseous and liquid components of the exhaust emissions. The analyzer system 10 has a liquid section 20 which draws the liquid components from the filter/separator 15 and passes them through a water filter 21 and a check valve 22 through a suction pump 23, and thence through a noise damper 24 to a liquid outlet. The gaseous components from the filter/separator 15 are fed through a gas filter 25 and then through a normally-open inlet port 26 of a solenoid valve 27, a normally-closed inlet port 28 of which receives ambient air which passes from an air inlet 29 through a charcoal filter 30 and a petrol filter 31.

The outlet port 32 of the valve 27 is coupled to a T-fitting 33, one leg of which is coupled through a flow restricter 34 to a vacuum sensor 35, and the other leg of which is coupled to the inlet of a pump 36. The outlet of the pump 36 is fed through a check valve 37 to a T-fitting 38, one leg of which receives calibration gas through a check valve 39. The T-fitting 38 is also coupled to an inlet of a condensate trap 40, the trap outlet of which is coupled through a conduit 41 to a gas outlet 42. The other outlet of the condensate trap 40 passes through a conduit 43 to a number of constituent sensors arranged in parallel.

More specifically, the conduit 43 is coupled to an oxygen sensor 44, the output of which is in turn coupled to the gas outlet 42. The conduit 43 is also coupled to an exhaust analyzer assembly 45, which may include a number of different sensors for sensing different constituents of the exhaust emissions, and may be of a known construction. The analyzer assembly 45 has an outlet which passes through a flow restricter 46 to one inlet of a T-fitting 47, the other inlet of which is coupled to the other outlet of the analyzer assembly 45, the outlet of the T-fitting 47, in turn, being connected to the gas outlet 42. The conduit 43 is also coupled through a flow reducer 48 and an inlet conduit 49 to a pulse dampening device 50, constructed in accordance with and embodying features of the present invention. The outlet of the pulse dampening device 50 is coupled through an outlet conduit 74 to an NO cell 75, the outlet of which is, in turn, connected to an NO outlet 76.

Figure 4:
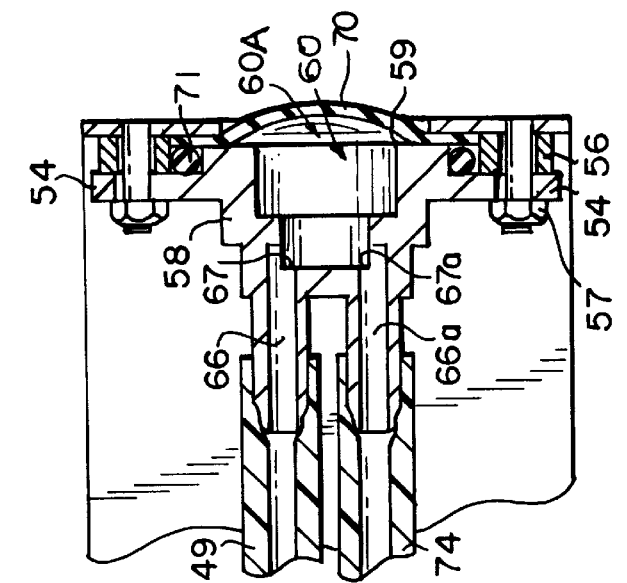
FIG. 4 is a view similar to FIG. 3, illustrating the membrane of the expansion chamber in the expanded condition.
Figure 3:
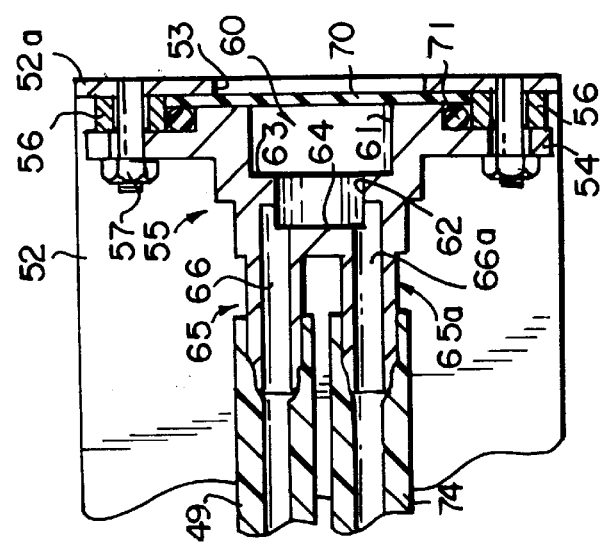
FIG. 3 is a sectional view taken along the line 3—3 in FIG. 2 with the membrane in its rest condition.
Figure 2:
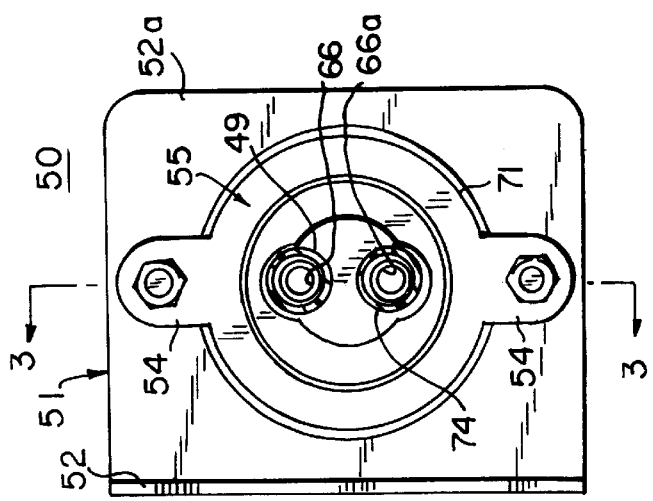
FIG. 2 is an enlarged bottom plan view of the expansion chamber of the system of FIG. 1.

Referring now also to FIGS. 2–4, the pulse dampening device 50 is supported on an angle bracket 51 including perpendicularly arranged walls 52 and 52A, the latter having a large circular opening 53 formed therethrough. Mounted on the wall 52A by means of attachment flanges 54 is a housing 55. More specifically, the attachment flanges 54 are spaced from the bracket wall 52A by bushings 56, the flanges 54 being attached to the bracket wall 52A by suitable threaded fasteners 57. The housing 55 has a generally cylindrical main body 58, which has a flat circular end wall 59, which has formed centrally therein a cylindrical cavity 60. The cavity 60 has a cylindrical inner surface 61 and communicates with a reduced-diameter cavity portion 62, being separated therefrom by an annular end wall 63. The reduced diameter portion 62 has a circular end wall 64.

The housing 55 has inlet and outlet ports 65 and 65A which, respectively, include cylindrical tubes 66 and 66A, which, respectively, receive over their distal ends the adjacent ends of the inlet and outlet conduits 49 and 74. The tubes 66 and 66A respectively communicate with the reduced diameter portion 62 of the cavity 60 through apertures 67 and 67A, which are formed respectively in the sides of the tubes 66 and 66A so as to communicate with only portions of the cross-sectional areas thereof.

The outer end of the cavity 60 is closed by an elastic membrane 70, which is preferably circular in shape and has marginal portions which are clamped between the bracket wall 52A and the end wall 59 of the housing 55. More particularly, an O-ring spacer 71 is disposed between the attachment flanges 54 and the membrane 70 which further enhances the seal between the outer cylindrical surface of the main body 58 of the housing and the membrane 70.

It will be appreciated that the membrane 70 cooperates with the cavity 60 to define an expansion chamber 60A of relatively small volume compared with the cross-sectional flow area of the inlet and outlet conduits 49 and 74. With each pulse or pressure surge in the gas stream caused by the pump 36, the membrane 70 stretches, as illustrated in FIG. 4, to expand the volume of the expansion chamber 60A, without a significant increase in pressure. When the surge passes, the membrane retracts to its original condition of FIG. 3, shrinking the volume of the expansion chamber 60A to its original volume. Thus, there is provided an expansion chamber 60A which has an initial relatively small capacity or volume, which affords a relatively rapid response time and, by reason of the elastic membrane 70, can increase to a relatively large volume, without a significant increase in pressure, depending upon the elastic value of the membrane 70. The change in volume of the expansion chamber 60A depends upon the area of the cavity 60 and the ambient outside air pressure. In this regard it is significant that the membrane 70 is not constrained, but has an outer surface which is exposed to the ambient air across the entire area of the opening 53.

Thus, there is achieved effective damping of the pump pulsations while maintaining sufficiently rapid response time of the nitric oxide sensing system in order to meet government regulations. If a rigid expansion chamber were utilized, it would have to have a much larger volume in order to achieve the same dampening effect, at the expense of an unacceptably slow response time.

In a constructional model of the invention, the membrane 70 may be formed of a suitable rubber or other suitable elastic material, and the housing of the expansion chamber may formed of any suitable rigid material, such as a suitable plastic. In a typical application, the mean pressure in the gas analyzer system 10 is close to atmospheric, so that there is no chance of blowing up the membrane 70 like a balloon.

From the foregoing, it can be seen that there has been provided an improved gas analyzer system and a pulse dampening device therefor which provides effective dampening of pulsations so as not to adversely affect an associated nitric oxide sensing cell, while achieving acceptably fast response times.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A system for analyzing constituents of exhaust emissions from an internal combustion engine comprising:
   a conduit adapted to be coupled to the engine for receiving exhaust emissions therefrom,
   a sensor for sensing a constituent of the emissions,
   a pump coupled to the conduit for moving the emissions through the conduit to the sensor, and
   a single expansion chamber coupled in the conduit and defined in part by an unconstrained, free-hanging elastic membrane having an inner surface exposed to the exhaust emissions and an outer surface exposed to ambient air for dampening pump-induced pulsations in the conduit, said chamber including structure supporting the membrane so that it is disposed generally normal to the direction of flow of exhaust emissions into the chamber.

2. The system of claim 1, wherein said sensor includes an electrochemical cell.

3. The system of claim 2, wherein said sensor includes a nitric oxide sensor.

4. The system of claim 1, wherein said expansion chamber is disposed between said pump and said sensor.

5. The system of claim 1, wherein said expansion chamber includes a housing defining a cavity with an open end and discrete inlet and outlet ports for communication with the conduit, said membrane cooperating with the housing to close the open end of the cavity.

6. The system of claim 5, wherein said housing includes a substantially cylindrical wall defining a side wall of said cavity.

7. The system of claim 5, wherein said housing includes two substantially cylindrical walls of different diameter joined by an annular wall and cooperating to form a side wall of said cavity.

8. The system of claim 5, wherein said membrane is substantially circular in shape, and further comprising a retaining plate cooperating with said housing to clamp said membrane therebetween around the periphery of said membrane.

9. The system of claim 5, wherein said housing includes substantially cylindrical tubular portions defining said ports.

10. The system of claim 9, wherein each of said ports communicates with said cavity along only a portion of the circumference of the tubular portion defining the port.

* * * * *